(12) United States Patent
Guo et al.

(10) Patent No.: US 12,097,375 B2
(45) Date of Patent: Sep. 24, 2024

(54) CARDIAC PACING SYSTEM AND PACEMAKER FIXING DEVICE

(71) Applicant: MICROPORT SOARING CRM (SHANGHAI) CO., LTD., Shanghai (CN)

(72) Inventors: Peng Guo, Shanghai (CN); Grace Jang, Shanghai (CN); Zhijun Cheng, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 855 days.

(21) Appl. No.: 17/279,349

(22) PCT Filed: Sep. 27, 2019

(86) PCT No.: PCT/CN2019/108331
§ 371 (c)(1),
(2) Date: Mar. 24, 2021

(87) PCT Pub. No.: WO2020/063793
PCT Pub. Date: Apr. 2, 2020

(65) Prior Publication Data
US 2021/0402193 A1  Dec. 30, 2021

(30) Foreign Application Priority Data
Sep. 27, 2018 (CN) .......................... 201811134030.6

(51) Int. Cl.
*A61N 1/375* (2006.01)
*A61N 1/362* (2006.01)

(52) U.S. Cl.
CPC ....... *A61N 1/37518* (2017.08); *A61N 1/3624* (2013.01); *A61N 1/37512* (2017.08); *A61N 1/37516* (2017.08); *A61N 1/3756* (2013.01)

(58) Field of Classification Search
CPC .............. A61N 1/37518; A61N 1/3624; A61N 1/37512; A61N 1/37516; A61N 1/3756;
(Continued)

(56) References Cited

U.S. PATENT DOCUMENTS

2002/0052645 A1* 5/2002 Kugler ...................... A61F 2/07
623/1.36
2003/0024534 A1* 2/2003 Silvestri ................... A61P 35/00
128/846
(Continued)

FOREIGN PATENT DOCUMENTS

CN 103284710 A 9/2013
CN 103381284 A 11/2013
(Continued)

*Primary Examiner* — Eugene T Wu
(74) *Attorney, Agent, or Firm* — MUNCY, GEISSLER, OLDS & LOWE, P.C.

(57) ABSTRACT

A cardiac pacing system and a pacemaker fixation device are disclosed. The pacemaker fixation device includes a ring-shaped stent and at least one contractible member. The ring-shaped stent is configured to load a leadless pacemaker and easily fix it at a target site in a patient's body reliably without dislodgement. A connecting element in the contractible member can be reliably connected to an external mechanism, thus facilitating retrieval and removal of the cardiac pacing system with an increased success rate. During implantation, the contractible member can be adapted by operating the external mechanism to adjust the pacing location for the leadless pacemaker, thus allowing the operator to easily determine the best pacing location that can result in enhanced pacing performance of the leadless pacemaker. Further, the leadless pacemaker may be fixed in the atrium in order to pace the atrium, thus reducing non-physiological pacing with atrioventricular desynchronization.

11 Claims, 4 Drawing Sheets

(58) Field of Classification Search
CPC .... A61N 1/362; A61N 1/37205; A61N 1/365; A61N 1/372
See application file for complete search history.

(56) References Cited

U.S. PATENT DOCUMENTS

| | | | |
|---|---|---|---|
| 2006/0259119 A1* | 11/2006 | Rucker | A61F 2/95 623/1.11 |
| 2009/0192585 A1 | 7/2009 | Bloom et al. | |
| 2012/0172891 A1 | 7/2012 | Lee | |
| 2014/0058494 A1 | 2/2014 | Ostroff et al. | |
| 2017/0326355 A1* | 11/2017 | Koop | A61B 5/686 |
| 2020/0146852 A1* | 5/2020 | Raychev | A61F 2/90 |

FOREIGN PATENT DOCUMENTS

| | | |
|---|---|---|
| CN | 103635160 A | 3/2014 |
| CN | 107949351 A | 4/2018 |
| CN | 108079437 A | 5/2018 |
| CN | 108310652 A | 7/2018 |
| CN | 207562016 U | 7/2018 |
| WO | WO-2013/035092 A2 | 3/2013 |

* cited by examiner

CARDIAC PACING SYSTEM AND PACEMAKER FIXING DEVICE

TECHNICAL FIELD

The present invention relates to the field of medical devices and, in particular, to a cardiac pacing system and a pacemaker fixation device.

BACKGROUND

Cardiac pacemakers are implantable therapeutic electronic devices incorporating an impulse generator for delivering electrical impulses which are transferred via leads to electrodes to stimulate the heart muscle, to which the electrodes are attached, thus causing the heart to be excited and contracted, thereby effecting treatment of heart dysfunction caused by some cardiac arrhythmia conditions. However, the use of lead cardiac pacemakers suffers from a high incidence of lead-related complications, presenting a serious threat to the life and health of patients. By contrast, leadless pacemakers integrate a battery, circuitry and pacing electrodes in a "compact capsule" that can be implanted into the heart simply via a percutaneous catheter, and have found extensive use in clinical practice thanks to a wide range of advantages including ease of operation, high convenience, minimal trauma, eliminated need for surgical creation of a pacemaker pocket, unaffected patients' appearance and absence of pacemaker pocket- or lead-related complications.

Existing leadless pacemakers can be implanted using a catheter and directly placed at various sites in the heart (right-heart placement, epicardial placement, etc.). At present, three leadless pacemakers that have been successfully developed include ultrasonic energy-mediated leadless pacemaker, electromagnetic energy-mediated leadless pacemaker and miniature leadless pacemaker. The three leadless pacemakers utilize different energy transmission mechanisms to deliver electrical impulses from the pacemaker to electrodes to stimulate the heart muscle. Miniature leadless pacemakers that have been put in clinical use are designed for direct fixation in and pacing of the right ventricle, and offer advantages including ease of operation, minimal invasiveness, no need for a pacemaker pocket and a reduced incidence of complications such as infection and vascular occlusion. However, such miniature leadless pacemakers are still associated with a number of disadvantages including: ventricular fixation without atrial pacing, leading to proneness of increased non-physiological pacing with atrioventricular desynchronization; a low success rate of removal and retrieval; and insufficient fixation firmness leading to proneness of dislodgement.

Therefore, it is necessary to develop a cardiac pacemaker system with direct atrial pacing and a pacemaker fixation device allowing easy retrieval of a leadless pacemaker, in order to overcome the disadvantages of existing leadless pacemakers.

SUMMARY OF THE INVENTION

It is an objective of the present invention to provide a cardiac pacing system and a pacemaker fixation device. The pacemaker fixation device is able to fix a leadless pacemaker in the superior vena cava (SVC) or at the SVC-right atrium (RA) junction so as to provide atrial pacing and hence dual-chamber pacing for the treatment of arrhythmia-caused cardiac dysfunction. Moreover, the pacemaker fixation device allows both reliable fixation and easy removal and retrieval of the leadless pacemaker.

To this end, the provided pacemaker fixation device includes:

a ring-shaped stent having opposing first and second ends; and at least one contractible member arranged at the first end of the ring-shaped stent, the contractible member including a connecting element and a plurality of contractible elements, the plurality of contractible elements disposed along a circumferential direction of the ring-shaped stent, all the contractible elements having first ends converging at and connected to the connecting element, the connecting element configured for detachable connection with an external mechanism, all the contractible elements having second ends connected to the first end of the ring-shaped stent, the first ends of the contractible elements arranged external to the first end of the ring-shaped stent in an axial direction of the ring-shaped stent, the contractible member configured to cooperate with the external mechanism to be contracted and folded when retracted by the external mechanism, which in turn contracts and folds the ring-shaped stent.

Optionally, the ring-shaped stent may include a body and at least one fixation member, each fixation member disposed at a respective one of a first end and/or an opposing second end of the body, the fixation member including a plurality of support struts arranged along the circumferential direction of the ring-shaped stent, all the support struts having first ends connected to the body and second ends connected to the contractible member, the fixation member arranged external to the body.

Optionally, the ring-shaped stent may include two fixation members, which are disposed at the respective opposing ends of the body and located external to the body.

Optionally, each fixation member may have a flared shape.

Optionally, the pacemaker fixation device may include two contractible members respectively arranged at the first and second ends of the ring-shaped stent.

Optionally, the connecting element may include a convex platform, which extends away from the ring-shaped stent and is configured at least for connection with a snare in the external mechanism.

Optionally, the convex platform may be arranged coaxial with the ring-shaped stent.

Optionally, the pacemaker fixation device may further include a fixation element, the fixation element having a first end disposed at one of the ends of the ring-shaped stent and a second end that is a free end configured to pierce into a target of implantation.

Optionally, the fixation element may be a barb or an anchor.

Optionally, the pacemaker fixation device may further include a graft, the graft surrounds an outer circumferential surface of the ring-shaped stent and has a hole formed therein, the hole configured to allow an electrode of a pacemaker to pass through.

In order to achieve the above objects, the provided cardiac pacing system includes a leadless pacemaker and the pacemaker fixation device as defined in any of the preceding paragraphs. The leadless pacemaker is disposed within the ring-shaped stent and connected to the ring-shaped stent, and the leadless pacemaker includes an electrode, which protrudes out of the ring-shaped stent along a radial direction of the ring-shaped stent.

Optionally, a lengthwise direction of the leadless pacemaker may be arranged along the axial direction of the ring-shaped stent.

In summary, the provided cardiac pacing system and pacemaker fixation device offers the following benefits:

First, the ring-shaped stent of the pacemaker fixation device is configured to load a leadless pacemaker and easily fix it in the SVC or on the SVC-RA junction, thus achieving atrial pacing and hence dual-chamber pacing, which can entail treatment of arrhythmia-caused cardiac dysfunction. In particular, the cardiac pacing system is fixed mainly in the atrium in order to provide atrial pacing by the leadless pacemaker, thus reducing non-physiological pacing with atrioventricular desynchronization.

Second, at least one end of the ring-shaped stent in the pacemaker fixation device is each additionally provided with a contractible member including a connecting element and contractible elements. All the contractible elements are gathered and connected to the connecting element at one end, making the contractible member appear like an umbrella. The connecting element can be easily connected to an external mechanism, and when the connecting element is retracted by the external mechanism, the umbrella-shaped contractible member will to be contracted and folded, which will in turn contract and fold the ring-shaped stent. In this way, removal, retrieval or re-positioning of the cardiac pacing system can be made easier, with an increased success rate. Specifically, in an implantation process, the connection between the connecting element and the external mechanism allows retrieval of the contractible member and hence adjustment in the pacing location for the leadless pacemaker, thus enabling the operator to quickly and easily determine the best pacing location that can result in enhanced pacing performance of the leadless pacemaker.

Third, in the pacemaker fixation device, at least one end of the body of the ring-shaped stent is each provided with a fixation member assuming a widened shape, which can increase radial support forces exerted on the ring-shaped stent when it is brought into contact with tissue of the patient. In this way, better prevention of displacement and dislodgement of the ring-shaped stent can be achieved, resulting in higher fixation reliability of the cardiac pacing system.

BRIEF DESCRIPTION OF THE DRAWINGS

The accompanying drawings are presented in order to provide a better understanding of the present invention without limiting it in any way. In these figures.

Figure 1:
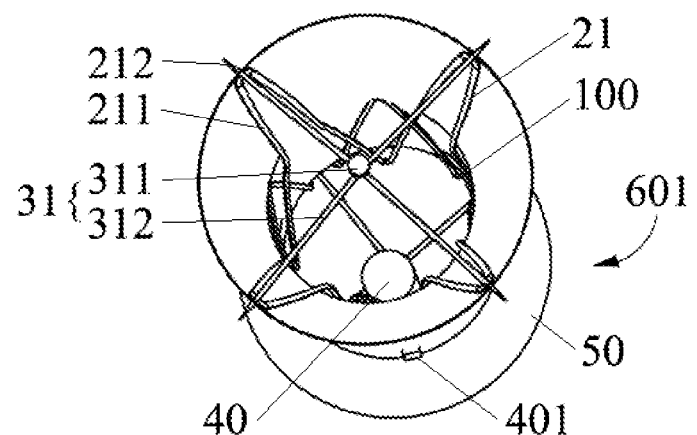
FIG. 1 is a perspective view of a cardiac pacing system according to an embodiment of the present invention.

In these figures, 10—ring-shaped stent; 100—body; 21—first fixation member; 211—first support strut; 221—second support strut; 212—fixation element; 22—second fixation member; 31—first contractible member; 311—first connecting element; 321—second connecting element; 312—first contractible element; 322—second contractible element; 32—second contractible member; 40—leadless pacemaker; 401—electrode; 50—graft; 601—cardiac pacing system; 602—right atrium (RA); 603—right ventricle; 604—inferior vena cava; 605—superior vena cava (SVC); 606—SVC—RA junction; 70—delivery sheath.

DETAILED DESCRIPTION

The core idea of the present invention is to provide a cardiac pacing system and a pacemaker fixation device. The pacemaker fixation device includes a ring-shaped stent and at least one contractible member, each including a connecting element and a number of contractible elements arranged along a circumferential direction. All the contractible elements have their first ends gathered at and connected to the connecting element. The connecting element is configured for detachable connection with an external mechanism. All the contractible elements have their second ends connected to one end of the ring-shaped stent, and in an axial direction of the ring-shaped stent, the gathered ends of the contractible elements are arranged external to said end of the ring-shaped stent. The contractible member is configured to cooperate with the external mechanism in such a manner that it contracts and folds when retracted by the external mechanism, thus causing the contraction and folding of the ring-shaped stent.

Here, the pacemaker fixation device is configured to fix a leadless pacemaker in the superior vena cava (SVC) or on the SVC-right atrium (RA) junction, thus achieving atrial pacing and hence dual-chamber pacing, which can entail treatment of arrhythmia-caused cardiac dysfunction. Moreover, the pacemaker fixation device allows reliable fixation and easy removal and retrieval of the leadless pacemaker.

The provided cardiac pacing system and pacemaker fixation device will be described in greater detail below by way of particular embodiments with reference to the accompanying drawings. Features and advantages of the invention will be more apparent from the following detailed description.

Note that the figures are provided in a very simplified form not necessarily drawn to scale, with the only intention to facilitate convenience and clarity in explaining the disclosed embodiments. In addition, structures shown in the figures are usually part of actual structures. In particular, as the figures tend to have distinct emphases, they are often drawn to different scales.

As used herein and in the appended claims, the singular forms "a", "an", and "the" include plural references unless the context clearly dictates otherwise. As used herein and in the appended claims, the term "or" is generally employed in its sense including "and/or" unless the content clearly dictates otherwise.

Figure 2:
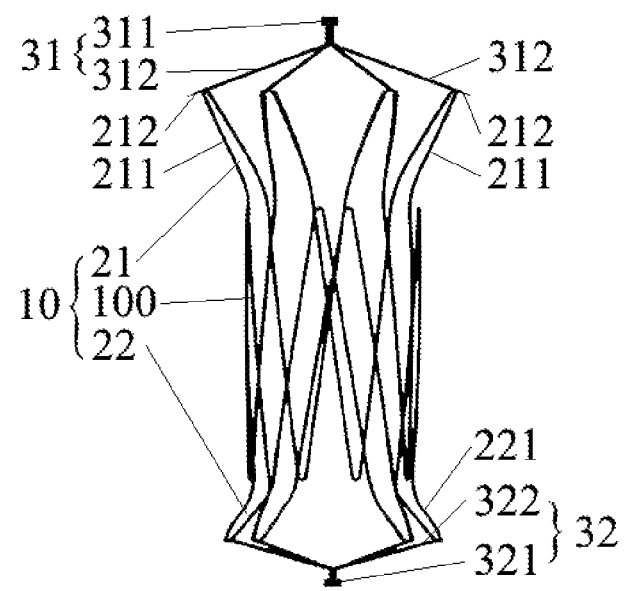
FIG. 2 is a front view of a pacemaker fixation device in the cardiac pacing system of FIG. 1, which does not include a graft.
Figure 3:
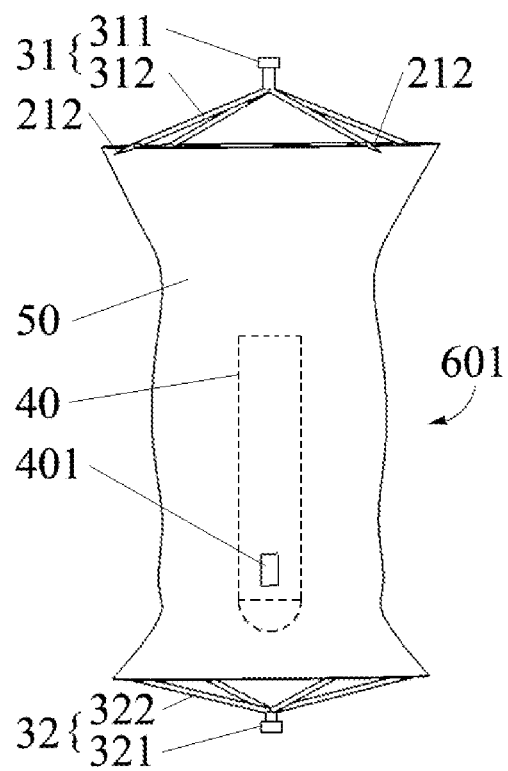
FIG. 3 is a front view of the cardiac pacing system of FIG. 1.
Figure 4:
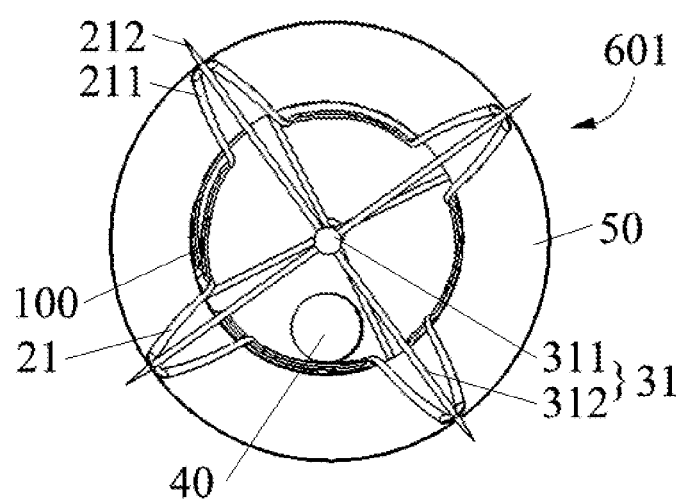
FIG. 4 is a top view of the cardiac pacing system of FIG. 1.
Figure 5:
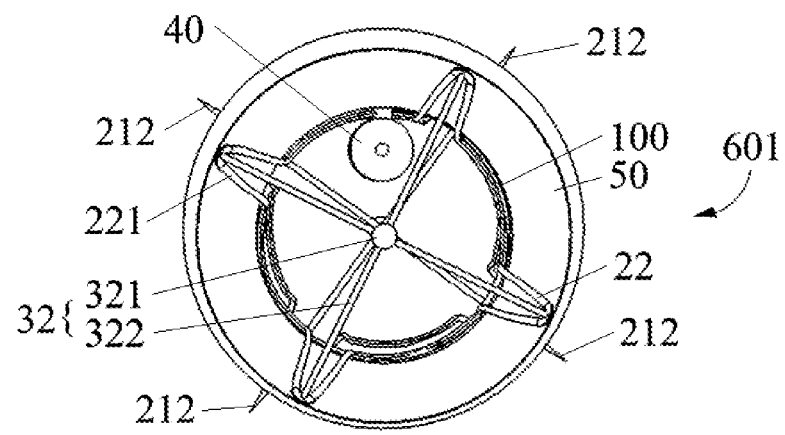
FIG. 5 is a bottom view of the cardiac pacing system of FIG. 1.
Figure 6:
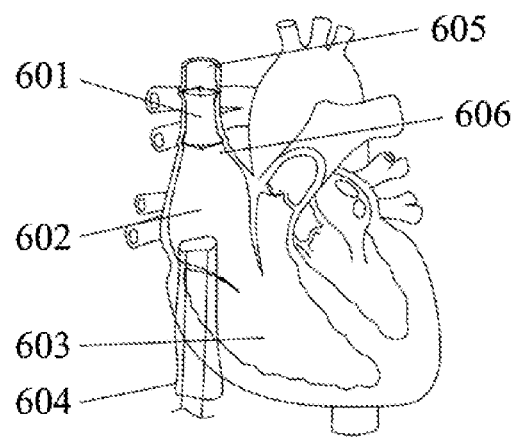
FIG. 6 is a diagram illustrating how the cardiac pacing system of FIG. 1 is implanted in the superior vena cava (SVC)
Figure 7:
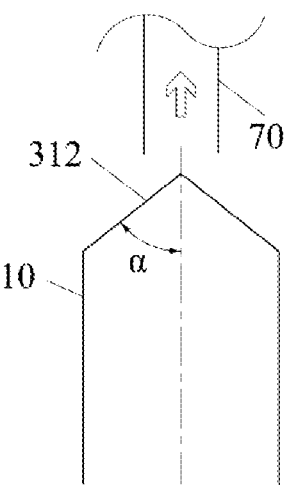
FIG. 7 is a schematic cross-sectional view of a first contractible member and a ring-shaped stent according to an embodiment of the present invention.
Figure 8:
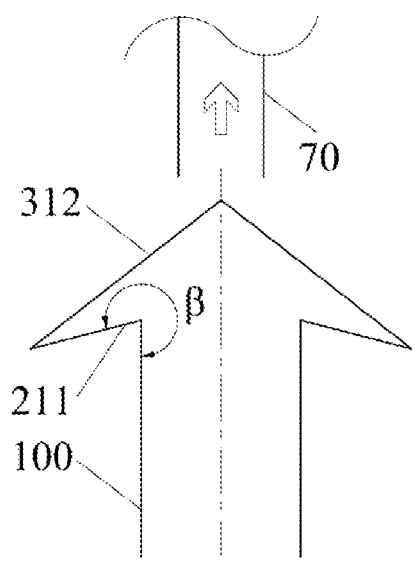
FIG. 8 is a schematic cross-sectional view of a first contractible member, a first fixation member and a body according to an embodiment of the present invention.

Reference is now made to FIGS. 1 to 8. FIG. 1 is a perspective view of a cardiac pacing system according to an embodiment of the present invention. FIG. 2 is a front view of a pacemaker fixation device in the cardiac pacing system of FIG. 1. FIG. 3 is a front view of the cardiac pacing system of FIG. 1. FIG. 4 is a top view of the cardiac pacing system of FIG. 1. FIG. 5 is a bottom view of the cardiac pacing system of FIG. 1. FIG. 6 is a diagram illustrating how the cardiac pacing system of FIG. 1 is implanted into the superior vena cava (SVC). FIG. 7 is a schematic cross-sectional view of a first contractible member and a ring-shaped stent according to an embodiment of the present invention. FIG. 8 is a schematic cross-sectional view of a first contractible member, a first fixation member and a body according to an embodiment of the present invention.

As shown in FIGS. 1 to 5, a cardiac pacemaker system 601 according to an embodiment of the present invention includes a leadless pacemaker 40 and a pacemaker fixation device (not shown). According to embodiments of the present invention, the pacemaker fixation device includes a ring-shaped stent 10 and a first contractible member 31. The ring-shaped stent 10 has two ends opposing each other. The first contractible member 31 is disposed at one end of the ring-shaped stent 10, and includes a first connecting element 311 and a number of first contractible elements 312. These first contractible elements 312 are distributed along a circumferential direction of the ring-shaped stent 10. Each of the first contractible elements 312 has opposing first and second ends. The first ends of all the first contractible elements 312 converge at and are connected to the first connecting element 311. The first connecting element 311 is configured for detachable connection with an external mechanism. The external mechanism may include, among others, a catheter, a guide wire, a snare and a delivery sheath. The first connecting element 311 may be configured for connection, in particular, with a guide wire or a snare. The second ends of all the first contractible elements 312 are connected to the ring-shaped stent 10, and in an axial direction of the ring-shaped stent 10, the converging ends of the first contractible elements 312 are arranged external to the end of the ring-shaped stent 10. The first contractible member 31 is configured to cooperate with the external mechanism in such a manner that it will be contracted and folded when retracted by the external mechanism, which will in turn contract and fold the ring-shaped stent 10. The external mechanism may include, among other, a delivery sheath and a guide wire. In use, the first contractible member 31 may be retracted by a guide wire, and when the first contractible member 31 comes into contact with a delivery sheath, it will be limited by opening edges of the delivery sheath. As a result, it may contract and fold, which will in turn cause the ring-shaped stent 10 to assume a folded and contracted configuration suitable for its reception in the delivery sheath.

Referring to FIG. 7, preferably, each of the first contractible elements 312 is elongated in shape and inclined at an angle α smaller than 90 degrees with respect to an axis of the ring-shaped stent 10. Here, the angle α may be, in particular, an angle of each first contractible element 312 formed with the axis (centerline) of the ring-shaped stent 10. The angle α of smaller than 90° between axes of each first contractible element 312 and the ring-shaped stent 10 can ensure that a retracting force exerted to the converging ends of the first contractible elements 312 in the axial direction of the ring-shaped stent 10 (indicated by the arrow in the figure) has components toward the axis of the ring-shaped stent 10. Therefore, pulling the first connecting element 311 by manipulating the external mechanism can, on the one hand, create force components on the first contractible elements 312 toward the centerline, which, together with the limiting effect of the delivery sheath, cause the contraction and folding of the first contractible member 31 and the ring-shaped stent 10, thus facilitating the removal and retrieval of the pacemaker fixation device, and on the other hand, ensure that the first contractible elements 312 will not be stuck on the delivery sheath. More preferably, the angle α does not exceed 60°, so that the retracting force can result in stronger components on the first contractible elements 312 toward the axis, which allow easier entry of the first contractible elements 312 into the delivery sheath. In addition, in practical use, the leadless pacemaker 40 may be loaded within the ring-shaped stent 10 in such a manner that it is connected to the ring-shaped stent 10. In this way, the leadless pacemaker 40 can be carried by the ring-shaped stent 10 to a target pacing site in the body of a patient and fixed at the site together with the stent.

In embodiments of the present invention, the ring-shaped stent 10 may be a self-expanding elastic stent made of, for example, superelastic Nitinol or the like, and the ring-shaped stent 10 can assume an expanded or folded configuration. The expanded configuration is a configuration in which ring-shaped stent 10 is free of stress and expands to the maximum extent that it can by virtue of its own elasticity. In this way, the ring-shaped stent 10 presses tightly against the wall of the blood vessel and is thus fixed within the blood vessel without displacement and dislodgement. In the folded configuration, the ring-shaped stent 10 is stressed and contracted, for example, by a compressive force toward its axis, and thus the ring-shaped stent 10 deforms toward the axis. This will in turn cause deformation of the first contractible member 31, making the fixation device appear as an elongated structure suitable for being received in the delivery sheath and delivered therewith by an external delivery system into the patient's body.

A method of use of the cardiac pacing system 601 of the present invention will be described below with reference to FIG. 6. As shown in FIG. 6, the leadless pacemaker 40 of the present invention is configured principally for fixation in the superior vena cava (SVC) 605 or at the SVC-RA junction 606, where it produces electrical impulses to stimulate the heart muscle around the SVC 605 or the SVC-RA junction 606, thus achieving atrial pacing. The atrial pacing signals will additionally propagate to the ventricle, further allowing dual-chamber pacing, which can entail treatment of bradycardia-caused cardiac dysfunction. According to embodiments of the present invention, the leadless pacemaker 40 may utilize an energy transmission mechanism like that of the existing miniature leadless pacemakers to transmit energy to an electrode brought into contact with the heart muscle so as to directly stimulate the heart muscle. In this way, pacing of the right atrium 602 can be achieved, thus reducing non-physiological pacing with atrioventricular desynchronization between the right atrium 602 and the right ventricle 603.

In embodiments of the present invention, the cardiac pacing system 601 may be, in particular, delivered by a delivery system into the SVC 605 or onto the SVC-RA junction 606. The delivery system may include, among others, a guide wire, a delivery sheath, a sheath core, a delivery shaft. Both the delivery shaft and the cardiac pacing system 601 may be inserted in the delivery sheath, with the connecting element in the pacemaker fixation device being connected to the delivery shaft. The delivery shaft may be configured to drive the cardiac pacing system 601 to move, as required by the delivery. The delivery system may be implemented as a conventional one that may be suitably selected by those skilled in the art.

According to one embodiment, the delivery of the cardiac pacing system can be accomplished by the delivery system in the manner detailed below.

In a first step, following percutaneous vein puncture and conventional right heart catheterization, the guide wire is introduced into the patient's body. In a second step, the delivery sheath and the sheath core in the delivery system are advanced along the guide wire into the SVC. In a third step, both the guide wire and the sheath core are withdrawn, with the delivery sheath being retained (in this process, particular attention must be paid to avoiding introducing the air into the patient's body; otherwise, coronary air embolism may occur). In a fourth step, the cardiac pacing system 601 is connected to the delivery shaft outside the patient's body, for example, by a threaded coupling between the delivery shaft and the first connecting element 311, and the cardiac pacing system 601 is then immersed in physiological saline and degassed for several times. In a fifth step, after the completion of the degassing, the cardiac pacing system 601 is placed into the delivery sheath. In a sixth step, the delivery shaft is pushed to advance the cardiac pacing system 601 in the delivery sheath to a target site in the SVC (here, during the advancement, attention must be paid to avoiding unintentional rotation of the delivery shaft, which may cause dislodgement of the cardiac pacing system 601). In a seventh step, with the aid of X-ray fluoroscopic monitoring on a monitor, for example, of a fluoroscopically viewable material of a body 100, a first fixation member 21, a second fixation member 22, the first contractible member 31 or the leadless pacemaker 40 in the cardiac pacing system 601, the cardiac pacing system 601 is pushed out of the delivery sheath at the target site. Upon release from the delivery sheath, the ring-shaped stent 10 will spontaneously expand by virtue of its own elasticity and press against the wall of the blood vessel. Concurrently, an electrode 401 will be pressed against the heart muscle, allowing atrial pacing of the leadless pacemaker 40 through delivering impulses.

Further, after the cardiac pacing system 601 is released from the delivery sheath, the delivery shaft may be maintained in connection with the cardiac pacemaker 601, and at the same time, pacing threshold and sensing amplitude monitoring of the leadless pacemaker 40 may be started, the pacing and sensing performance of the leadless pacemaker 40 may be determined according to the pacing threshold and the sensing amplitude. If it is determined that the pacing and sensing performance is unsatisfactory, the delivery shaft and the delivery sheath may be manipulated to entirely or partially retrieve the cardiac pacing system 601 into the delivery sheath and then release it to a different position. This process can be repeated until the cardiac pacing system 601 is released to a desired position. After that, the delivery shaft may be disconnected from the cardiac pacing system 601, for example, by disengaging the threaded coupling of the cardiac pacing system 601 and the delivery shaft through turning the delivery shaft. With this done, both the delivery shaft and the delivery sheath may be withdrawn from the venous vascular system, thus ending the leadless pacemaker implantation process.

In use, the ring-shaped stent 10 presses against the wall of the SVC 605 by means of its own elasticity. As a result, radial support forces from the blood vessel wall retain the ring-shaped stent 10 within the SVC 605 in a manner without displacement and dislodgement (in the axial direction) of the ring-shaped stent 10. Moreover, during re-positioning of the ring-shaped stent 10, the delivery shaft may be pulled backwards to retract the umbrella-shaped first contractible member 31 so that the ring-shaped stent 10 will be radially reduced in size and move away from the contact with the blood vessel wall (this may further cause detachment of the fixation element 212 detailed below from the tissue of the blood vessel wall). In this way, it can be retrieved into the delivery sheath more easily.

In addition, in the pacemaker fixation device according to embodiments of the present invention, an umbrella-shaped first contractible member 31 is added to at least one end of the ring-shaped stent 10, the first connecting element 311 in the umbrella-shaped first contractible member 31 can be reliably connected to the external mechanism. This facilitates the removal, retrieval and re-positioning of the cardiac pacing system 601 with the aid of the first contractible member 31 and allows an increased success rate of removal, retrieval and re-positioning for the cardiac pacemaker system 601. During the implantation process, retrieval of the first contractible member 31, which relies mainly on the connection between the first connecting element 311 and the external mechanism, allows adjustment in the pacing location for the leadless pacemaker. In this way, the operator can quickly and easily determine the best pacing location that can result in enhanced pacing performance of the leadless pacemaker 40.

A more detailed description of the structure of the pacemaker fixation device will be set forth below with continued reference to FIGS. 2 to 5.

Reference is first made to FIG. 2. According to one preferred embodiment, the ring-shaped stent 10 may include a body 100 and a first fixation member 21 disposed at one end of the body 100. The body 100 may be ring-shaped. The first fixation member 21 may include a number of first support struts 211 arranged along a circumferential direction of the body 100. Preferably, these first support struts 211 are evenly distributed along the circumferential direction (i.e., evenly distributed around the body 100). Each first support strut 211 may have opposing third and fourth ends. The third ends of all the first support struts 211 may be connected to one end of the body 100, and the fourth ends of all the first support struts 211 may be connected to the first contractible member 31. Moreover, the first fixation member 21 may be located external to the body 100. Here, the term "externally" is meant to mean that, except for the part connected to the body 100, the entire first fixation member 21 extends outside the body 100 of the ring-shaped stent 10, rather than inside the body 100. Further, each first support strut 211 may form an angle β of greater than 90° with a side wall of the body 100 (more precisely, an internal surface of the side wall of the body 100), which facilitates contraction and folding of the first fixation member 21 upon the first contractible member 31 being retracted by the external mechanism. Preferably, the angle β formed by each first support strut 211 and (the internal surface of) the side wall of the body 100 is greater than 120°, so that the first contractible member 31 can cause smoother contraction and folding of the first fixation member 21. For example, as shown in FIG. 8, the angle β may be equal to 280°. The first contractible elements 312 in the first contractible member 31 can also cause contraction and folding of the first support struts 211 in the first fixation member 21. Specifically, the fourth ends of the first support struts 211 may be connected to the second ends of the first contractible elements 312 in the first contractible member 31 in such a manner that each first contractible element 312 may be connected to one or more of the first support struts 211. In one embodiment, the first fixation member 21 may be configured to increase the radial support forces exerted by the wall of the blood vessel on the ring-shaped stent 10 after the whole cardiac pacing system 601 has been fixed in the target site in the blood vessel. In this way, the ring-shaped stent 10 will not slide axially, and even minimal displacement or dislodgement of the cardiac pacing system 601 can be thus prevented. Preferably, the body 100 is integrally formed with the first fixation member 21, for example, by braiding, cutting or the like.

Specifically, the first fixation member 21 may also be an elastic structure made of, for example, superelastic Nitinol or the like. Angles between the first support struts 211 and between them and the body 100 may change as a function of a stress condition. When the ring-shaped stent 10 is free of stress and in the expanded configuration, the first support struts 211 will also assume an expanded configuration where they stretch under the action of the elasticity of themselves and of the body 100. In this configuration, the first fixation member 21 is preferred to assume a widened or flared shape (i.e., having a diameter increasing from the end coupled to the body 100; or having a projected diameter on a plane parallel to end faces of the first fixation member 21 increasing from the end face delimited by the third ends of all the first support struts 211 in the first fixation member 21 to the end face delimited by the fourth ends of all the first support struts 211 in the first fixation member 21), and a minimum diameter of the first fixation member 21 is equal to a diameter of the body 100. In other words, all the first support struts 211 may extend from the third ends outwardly with respect to the body 100 so that the angle β between the first support struts 211 and the side wall of the body 100 (both the side wall of the body 100 and the internal surface thereof) are greater than 180°. Because of the diameter of the first fixation member 21 increasing from the end connected to the body 100, the ring-shaped stent 10 in the expanded configuration can be fixed at the target site in the blood vessel by means of stable radial support forces provided by the wall of the blood vessel to the ring-shaped stent 10, thus effectively preventing even minimal displacement or dislodgement of the pacemaker fixation device. In alternative embodiments, as long as the wall of the blood vessel can provide sufficient radial support forces to the ring-shaped stent 10 that is being fixed at the target site, the first fixation member 21 may also assume a straight tubular shape having a constant diameter. That is, the diameter of the first fixation member 21 at the end connected to the body 100 is the same as the remainder. Speaking differently, the diameter of the first fixation member 21 is equal to the diameter of the body 100.

Preferably, the first support struts 211 are U- or V-shaped, with their third ends that are connected to one end of the body 100 defining an opening, and with the fourth ends of the first support struts 211 that are connected to the first contractible member 31 being connected to one another and thus defining a closed configuration. In this way, portions around the fourth ends can have curved contact surfaces with the blood vessel wall or other tissue, which are more favorable to protecting the blood vessel wall or tissue from damage, when compared to the case using a single support element. The curvature of the U- or V-shaped first support struts 211 may be adjusted to adapt the entire first fixation member 21 to a radial size enabling the wall of the blood vessel to provide desirable radial support forces to the ring-shaped stent 10 fixed at the target site. Additionally, the radial support forces exerted by the wall of the blood vessel on the ring-shaped stent 10 that is being fixed at the target site can also be directly adjusted by means of the angle formed between the first support struts 211 and the body 100. Folding and expansion can be made easier by varying the curvature of the U- or V-like shape and the angle formed with the body 100. Alternatively, the first support struts 211 may also be otherwise shaped, for example, X-, I- or Y shaped, and in these cases, they can still provide the adjustability in the radial support forces exerted by the wall of the blood vessel on the ring-shaped stent 10 that is being fixed at the target site, as well as easier folding and expansion. The present invention is not limited to any particular shape of the first support struts 211.

As shown in FIG. 2, in one preferred embodiment, such fixation members are arranged on respective opposing ends of the body 100 of the ring-shaped stent 10. This can not only provide excellent structural integrity, but also enables more firm support of the whole structure without displacement or dislodgement of the stent during the retrieval and release processes for the cardiac pacing system 601. Specifically, in addition to the first fixation member 21 arranged at one end of the body 100, the ring-shaped stent 10 may further include a second fixation member 22 arranged on the other end of the body 100. The second fixation member 22 may include a number of second support struts 221, these second support struts 221 are arranged along the circumferential direction of the body 100. Each second support strut 221 may have opposing fifth and sixth ends. The fifth ends of all the second support struts 221 may be connected to the other end of the body 100. Preferably, the second fixation member 22 is structured in the same way as the first fixation member 21. More preferably, the second fixation member 22 may also assume a widened or flared shape (i.e., having a diameter increasing from the end coupled to the other end of the body 100; or having a projected diameter on a plane parallel to end faces of the second fixation member 22 increasing from the end face delimited by the fifth ends of all the second support struts 221 in the second fixation member 22 to the end face delimited by the sixth ends of all the second support struts 221 in the second fixation member 22). Alternatively, the second fixation member 22 may also assume a straight tubular shape (i.e., having a diameter that is equal to the diameter of the body 100). Here, portions around the sixth ends can have curved contact surfaces with the blood vessel wall or other tissue, which are more favorable to protecting the blood vessel wall or tissue from damage, when compared to the case using a single support element. Likewise, the second fixation member 22, in particular, in the widened shape, can also increase the radial support forces provided by the wall of the blood vessel to the ring-shaped stent 10. The sixth ends of the second support struts 221 can be free ends that do not connect any other component. Preferably, the body 100 is further integrally formed with the second fixation member 22. Optionally, the body 100 may not be integrated with the fixation members. Rather, it may be separately fabricated from them and then connected thereto, for example, by welding or bonding. The present invention is not limited in this regard.

Preferably, the pacemaker fixation device further includes a second contractible member 32 disposed at the other end of the ring-shaped stent 10 that opposes the end where the first contractible member 31 is arranged. Specifically, the second contractible member 32 may include a second connecting element 321 and a number of second contractible elements 322 arranged along the circumferential direction. The second contractible elements 322 may be elongated structures, and the second contractible elements 322 are all gathered and connected to the second connecting element 321 at one end. The second connecting element 321 may be configured for detachable connection with the external mechanism, and the other ends of all the second contractible elements 322 may be connected to the other end of the ring-shaped stent 10. Moreover, in the axial direction of the ring-shaped stent 10, the ends of the second contractible elements 322 where they are gathered may be situated external to the other end of the ring-shaped stent 10.

Preferably, the second contractible member 32 may have the same structure as the first contractible member 31. In this case, the sixth ends of the second support struts 221 may be connected to the second contractible member 32 in a similar way in which the first support struts 211 are connected to the first contractible member 31.

Referring to FIG. 6, providing the second contractible member 32 allows the external mechanism to access the target site either from the inferior vena cava (IVC) 604 or from the SVC 605, during the implantation and removal processes for the cardiac pacing system 601. This two-way operation makes the implantation and removal even easier.

In one embodiment, the pacemaker fixation device may further include fixation element 212. One end of the fixation element 212 may be arranged at one end of the ring-shaped stent 10, and the other end of the fixation element 212 may be a free end configured to pierce a tissue, e.g., the wall of a blood vessel. Here, the phrase "arranged at one end of the ring-shaped stent 10" shall not be interpreted narrowly as having to be arranged on the corresponding end face of the ring-shaped stent 10. For example, "arranging the fixation element 212 at the end of the ring-shaped stent 10 where it is connected to the first contractible member 31" shall be interpreted broadly as arranging it in a region of the ring-shaped stent 10 close to the first contractible member 31. Particularly, the fixation element 212 may be connected at one end to the ring-shaped stent 10, with the other end extending away from the axis of the ring-shaped stent 10. That is, the fixation element 212 may extend outwardly from the ring-shaped stent 10.

Similarly, when used to describe the ring-shaped stent 10, the term "radial" is meant to refer to a direction that is not limited to being perpendicular to the axis of the ring-shaped stent 10. Rather, it may refer to a direction inclined, but not parallel, to the axis. The end of the fixation element 212 extending outwardly from the ring-shaped stent 10 is configured to pierce into the wall of the blood vessel or into the heart muscle at the target site when the cardiac pacing system 601 is fixed at the target site. This can provide additional radial support forces to the cardiac pacing system 601, thus enabling effective prevention of any minimal displacement or dislodgement of the cardiac pacing system 601 in the axial direction. During removal or retrieval of the cardiac pacing system 601, the fixation element 212 can be easily pulled out from the target site, with reduced damage to the wall of the blood vessel or the heart muscle. Preferably, the fixation element 212 is inclined toward the first connecting element 311. This can facilitate the fixation to the wall of the blood vessel at the target site and allows the removal of the whole cardiac pacing system 601 from the target site with a reduced angle change. Additionally, the fixation element 212 may be received in the delivery sheath together with the ring-shaped stent 10, thus additionally reducing damage to the wall of the blood vessel. Preferably, the fixation element 212 may be a barb or an anchor, each of which can firmly engage with the blood vessel wall or heart muscle and be easily removed therefrom. Preferably, a plurality of such fixation element 212 are provided, and the plurality of fixation element 212 are preferably arranged evenly along the circumferential direction (i.e., evenly distributed around the ring-shaped stent 10).

It is to be noted that the fixation element 212 may be arranged at either one or both ends of the ring-shaped stent 10. In the case of being arranged at both ends of the ring-shaped stent 10, it is preferred that the fixation element 212 at the both ends of the ring-shaped stent 10 are inclined in the same direction, with the free ends of the fixation element 212 extending in a direction opposite to the direction of removal of the cardiac pacing system 601. In this way, the fixation element 212 can be easily pulled off during the removal and retrieval of the cardiac pacing system 601, while bringing reduced damage to the wall of the blood vessel. For example, in the case in which the external mechanism is delivered via the IVC 604 to remove or retrieve the cardiac pacing system, the fixation element 212 may be arranged on the end farther away from the right atrium or on both ends, with the free ends of the fixation element 212 inclined away from the IVC 604. In the case in which the external mechanism is delivered via the SVC 605 to remove or retrieve the cardiac pacing system, the fixation element 212 may be arranged on the end closer to the right atrium or on both ends, with the free ends of the fixation element 212 inclined away from the SVC 605.

The pacemaker fixation device may further include a graft 50, which surrounds an outer circumferential surface of the ring-shaped stent 10. Moreover, the graft 50 defines a hole for the passage of an electrode 401 of the leadless pacemaker 40 therethrough. Preferably, the graft 50 is flush with the ring-shaped stent 10 at both ends. The graft 50 can increase a contact area of the ring-shaped stent 10 with the inner wall of the SVC 605 or with the SVC-RA junction 606 and reduce the damage to the inner wall. In case of the cardiac pacing system 601 being intended for long-term deployment, the graft 50 can slow down wrapping of the ring-shaped stent 10 and hence of the pacemaker 40 by the inner wall of the SVC 605, the SVC-RA junction 606 or hyperplastic tissue therein. Therefore, the graft 50 can slow down wrapping of the pacemaker 40 by the inner wall of the SVC 605, the SVC-RA junction 606 or hyperplastic tissue therein. This facilitates separation, removal and retrieval of the pacemaker 40 from the inner wall of the SVC 605 or from the SVC-RA junction 606 after the cardiac pacing system 601 has been deployed for a designed long term.

In embodiments of the present invention embodiment, the electrode 401 may be attached to a side wall of the leadless pacemaker 40 and the electrode 401 preferably protrudes out of the ring-shaped stent 10 along the radial direction of the ring-shaped stent 10. Moreover, the electrode 401 may protrude out of the ring-shaped stent 10 via the hole in the graft 50. The graft 50 may be formed of an insulating material, and the outer circumferential surface of the ring-shaped stent 10 may be pressed against the inner wall of the SVC 605 or the SVC-RA junction 606. Therefore, the pacing electrode 401 protruding out of the ring-shaped stent 10 through the graft 50 will be brought into direct contact with and pressed against the heart muscle at the SVC 605 or SVC-RA junction 606 by the ring-shaped stent 10. In this way, it may accomplish reliable delivery of electrical signals.

Preferably, the leadless pacemaker 40 may be a cylinder or prism having an axial length greater than or equal to its diameter. An axial direction of the leadless pacemaker 40 is preferably arranged along the axial direction of the ring-shaped stent 10. In this way, during delivery of the cardiac pacemaker system 601, the ring-shaped stent 10 can be contracted and shrink in size as much as possible, and such contraction of the ring-shaped stent 10 will not be hindered by the leadless pacemaker 40. In particular, the arrangement of the axial direction of the leadless pacemaker 40 along that of the ring-shaped stent 10 shall be broadly interpreted as a non-perpendicular arrangement of the axial direction of the leadless pacemaker 40 with respect to that of the ring-shaped stent 10. Additionally, an angle may be formed between the axial direction of the leadless pacemaker 40 and the axial direction of the ring-shaped stent 10, as long as it ensures that the direction in which the whole leadless pacemaker 40 has a maximum dimension is along the axial direction of the ring-shaped stent 10.

Optionally, the first connecting element 311 may be connected to the external mechanism by means of threads, a spring latch, a snare or a snap fastener. Preferably, the first connecting element 311 includes a convex platform extending away from the ring-shaped stent 10. Specifically, the convex platform may consist of two diametrically different, coaxial cylinders joined to each other. Preferably, the convex platform extends along the axial direction of the ring-shaped stent 10. The diametrically larger cylinder may be arranged farther away from the ring-shaped stent 10 and have a diameter smaller than that of the ring-shaped stent 10 in the folded configuration. Preferably, a thread may be formed in its outer circumferential surface. The cylinder having smaller diameter may be arranged closer to the ring-shaped stent 10, and the first ends of the first contractible elements 312 may be all connected to this cylinder with smaller diameter. The thread in the convex platform is configured to engage with the delivery shaft in the external mechanism during the implantation process of the cardiac pacing system 601, thereby providing a securing effect. Upon delivery to the target site, the two may be disengaged by turning the delivery shaft. The convex platform is so configured that an external snare can be easily looped and tightened thereon during the removal of the cardiac pacing system 601. It is also configured to subsequently cooperate with the delivery sheath to receive the cardiac pacing system 601 therein. In this way, reliable removal and retrieval of the cardiac pacing system 601 can be achieved. The structure and the expanded and folded configurations of the second contractible member 32 are substantially the same as those of the first contractible member 31.

With the case of removing the cardiac pacing system 601 by retracting the first contractible member 31 as an example, after the external snare is looped and tightened over the convex platform, the external mechanism may be manipulated to cause the convex platform to move proximally toward the operator along the axial direction. Since the diameter of the first contractible member 31 in the expanded configuration is greater than a diameter of the delivery sheath, the first contractible member 31 will be resisted by the opening edge of the delivery sheath and experience distally-acting forces therefrom. As a result, the first contractible member 31 will fold like an umbrella until it is entirely received in the delivery sheath. Moreover, since the second ends of the first contractible elements 312 are connected to the ring-shaped stent 10, the ring-shaped stent 10 will fold with the folding of the first contractible member 31 and be pulled into the delivery sheath under the action of further backward movement of the external mechanism. Subsequently, the second contractible member 32 will fold and be pulled into the delivery sheath in a similar style. It would be appreciated by those skilled in the art that when the entire cardiac pacing system 601 has been received in the delivery sheath, it can be smoothly withdrawn from the patient's body. Apparently, the snare in the external mechanism may also be looped and tightened over the convex platform of the second contractible member 32, and the cardiac pacing system 601 may also be removed by retracting the second contractible member 32 in a similar manner.

In order for uniform force transmission and easy removal and retrieval to be achieved, the two cylinders that make up the convex platform are arranged coaxial with the ring-shaped stent 10. Specifically, during implantation and removal of the cardiac pacing system 601, a point of force application of the external mechanism to the cardiac pacing system 601 may be on the axis of the cardiac pacing system 601. In this way, uniform force distribution may take place over the above-described various coaxial-arranged components, enhancing the preciseness of the implantation and removal operations.

In summary, although a number of preferred embodiments of the present invention have been described hereinabove, the scope of the invention is not limited to these disclosed embodiments. For example, the first contractible member may be structured either identically to or differently from the second contractible member, and the first and second fixation members may have either the same structure or different structures. It will be appreciated that, according to the present invention, it is possible that at least one end of the ring-shaped stent is each provided with one contractible member (the first or second contractible member), and it is preferred that contractible members (the first and second contractible members) are arranged at the respective opposing ends of the ring-shaped stent. It will be also appreciated that, according to the present invention, it is possible that at least one end of the body of the ring-shaped stent is each provided with one fixation member (the first or second fixation member), and it is preferred that fixation members (the first and second fixation members) are arranged at the respective opposing ends of the body.

Compared with the prior art, the cardiac pacing system and pacemaker fixation device according to embodiments of the present invention offer the following advantages:

First, the pacemaker fixation device is configured to load a leadless pacemaker and easily fix it in the SVC or on the SVC-RA junction, thus achieving atrial pacing and hence dual-chamber pacing, which can entail treatment of arrhythmia-caused cardiac dysfunction.

Second, the cardiac pacing system is fixed mainly in the atrium in order to provide atrial pacing by the leadless pacemaker, thus reducing non-physiological pacing with atrioventricular desynchronization.

Third, at least one end of the ring-shaped stent in the pacemaker fixation device is each additionally provided with an umbrella-shaped contractible member having a connecting element to which an external mechanism can be reliably connected. The contractible member allows easy removal, retrieval or re-positioning of the cardiac pacing system with an increased success rate. Specifically, in an implantation process, the connection between the connecting element and the external mechanism allows retrieval of the contractible member and hence adjustment in the pacing location for the leadless pacemaker, thus enabling the operator to quickly and easily determine the best pacing location that can result in enhanced pacing performance of the leadless pacemaker.

Fourth, in the pacemaker fixation device, at least one end of the body of the ring-shaped stent is each provided with a fixation member assuming a widened shape, which can increase radial support forces exerted on the ring-shaped stent when it is brought into contact with tissue of the patient. In this way, better prevention of displacement and dislodgement of the ring-shaped stent can be achieved, resulting in higher fixation reliability of the cardiac pacing system.

It is to be noted that the description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. A pacemaker fixation device, comprising:
a ring-shaped stent having opposing first and second ends; and
at least one contractible member arranged at the first end of the ring-shaped stent, the contractible member comprising a connecting element and a plurality of contractible elements, the plurality of contractible elements disposed along a circumferential direction of the ring-shaped stent, all the contractible elements having first ends converging at and connected to the connecting element, the connecting element configured for detachable connection with an external mechanism, all the contractible elements having second ends connected to the first end of the ring-shaped stent, the first ends of the contractible elements arranged external to the first end of the ring-shaped stent in an axial direction of the ring-shaped stent, the contractible member configured to cooperate with the external mechanism to be contracted and folded when retracted by the external mechanism, which in turn contracts and folds the ring-shaped stent,
wherein the ring-shaped stent comprises a body and at least one fixation member, each fixation member disposed at a respective one of a first end and/or an opposing second end of the body, the fixation member comprising a plurality of support struts arranged along the circumferential direction of the ring-shaped stent, all the support struts having first ends connected to the body and second ends connected to the contractible member, the plurality of support struts arranged external to the body, causing the contraction and folding of the fixation member when the contractible member is retracted by the external mechanism.

2. The pacemaker fixation device of claim 1, wherein the ring-shaped stent comprises two fixation members, which are disposed at the respective opposing ends of the body and located external to the body.

3. The pacemaker fixation device of claim 1, wherein each fixation member has a flared shape.

4. The pacemaker fixation device of claim 1, wherein the pacemaker fixation device comprises two contractible members respectively arranged at the first and second ends of the ring-shaped stent.

5. The pacemaker fixation device of claim 1, wherein the connecting element comprises a convex platform, which extends away from the ring-shaped stent and is configured at least for connection with a snare in the external mechanism.

6. The pacemaker fixation device of claim 5, wherein the convex platform is arranged coaxial with the ring-shaped stent.

7. The pacemaker fixation device of claim 1, further comprising a fixation element, the fixation element having a first end disposed at one of the ends of the ring-shaped stent and a second end that is a free end configured to pierce into a target of implantation.

8. The pacemaker fixation device of claim 7, wherein the fixation element is a barb.

9. The pacemaker fixation device of claim 1, further comprising a graft, the graft surrounding an outer circumferential surface of the ring-shaped stent and having a hole formed therein, the hole configured to allow an electrode of a pacemaker to pass through.

10. A cardiac pacing system, comprising a leadless pacemaker and the pacemaker fixation device of claim 1, the leadless pacemaker disposed within the ring-shaped stent and connected to the ring-shaped stent, wherein the leadless pacemaker comprises an electrode, which protrudes out of the ring-shaped stent along a radial direction of the ring-shaped stent.

11. The cardiac pacing system of claim 10, wherein a lengthwise direction of the leadless pacemaker is arranged along the axial direction of the ring-shaped stent.

* * * * *